US012252526B2

United States Patent
Xue et al.

(10) Patent No.: US 12,252,526 B2
(45) Date of Patent: Mar. 18, 2025

(54) TCR-ENRICHED CLONOTYPE, ACQUISITION METHOD AND USE THEREOF

(71) Applicant: HUNAN YUANPIN CELL TECHNOLOGY CO. LTD., Hunan (CN)

(72) Inventors: Zhigang Xue, Hunan (CN); Jinfeng Xue, Hunan (CN); Ning Yi, Hunan (CN); Bo Lv, Hunan (CN); Chanyi Li, Hunan (CN); Lingbin Qi, Hunan (CN); Weilin Li, Hunan (CN)

(73) Assignee: HUNAN YUANPIN CELL TECHNOLOGY CO. LTD., Changsha (CN)

( * ) Notice: Subject to any disclaimer, the term of this patent is extended or adjusted under 35 U.S.C. 154(b) by 661 days.

(21) Appl. No.: 17/475,686

(22) Filed: Sep. 15, 2021

(65) Prior Publication Data

US 2021/0403529 A1 Dec. 30, 2021

Related U.S. Application Data

(63) Continuation-in-part of application No. PCT/CN2020/105806, filed on Jul. 30, 2020.

(30) Foreign Application Priority Data

| May 23, 2020 | (CN) | 202010444541.9 |
| May 23, 2020 | (CN) | 202010444542.3 |
| May 23, 2020 | (CN) | 202010444546.1 |
| May 23, 2020 | (CN) | 202010444548.0 |
| May 23, 2020 | (CN) | 202010445718.7 |

(51) Int. Cl.
*C07K 14/725* (2006.01)
*A61K 39/00* (2006.01)

(52) U.S. Cl.
CPC .......... *C07K 14/7051* (2013.01); *A61K 39/00* (2013.01)

(58) Field of Classification Search
None
See application file for complete search history.

(56) References Cited

FOREIGN PATENT DOCUMENTS

| CN | 102212888 A | 10/2011 |
| CN | 107636152 A | 1/2018 |

OTHER PUBLICATIONS

Fischer et al., Mol Syst Biol (2020) 16:e9416. (Year: 2020).*
Mysore et al. (Med 2, 1050-1071, published Sep. 10, 2021). (Year: 2021).*
International Search Report from corresponding International Application No. PCT/CN2020/105806 mailed on Jan. 28, 2021, 5 pages.
Rosati, Elisa, et al., "Overview of methodologies for T-cell receptor repertoire analysis", BMC Biotechnology, (2017), 16 pages.
Chen, Guobing, et al., "Sequence and Structural Analyses Reveal Distinct and Highly Diverse Human CD8+ TCR Repertoires to Immunodominant Viral Antigens", Cell Reports 19, Apr. 2017, pp. 569-605.
Billam, Padma, et al., "T Cell Receptor Clonotype Influences Epitope Hierarchy in the CD8+ T Cell Response to Respiratory Syncytial Virus Infection", The Journal of Biological Chemistry, Feb. 2011, vol. 286, No. 6, pp. 4829-4841.

* cited by examiner

*Primary Examiner* — Zachary S Skelding
(74) *Attorney, Agent, or Firm* — Tucker Ellis LLP

(57) ABSTRACT

Disclosed are TCR-enriched clonotypes, and an acquisition method and use thereof. Amino acid sequences of the TCR-enriched clonotypes are: CAANRGSGYSTLTF (SEQ ID NO: 1)_CSARGERGEKLFF (SEQ ID NO: 2), CASSSGGSYIPTF (SEQ ID NO: 3)_CASSLAGGHETQYF (SEQ ID NO: 4), CAVNSYN-TDKLIF (SEQ ID NO: 5)_CATSREEDNTYEQYF (SEQ ID NO: 6), CAVGGNEKLTF (SEQ ID NO: 7)_CASSQGT-GRSSPLHF (SEQ ID NO: 8), or CAASAVGGAQKLVF (SEQ ID NO: 9)_CATSRGTLYGYTF (SEQ ID NO: 10), respectively. The TCR-enriched clonotypes can be used for vaccine development.

2 Claims, 6 Drawing Sheets

Specification includes a Sequence Listing.

SEQUENCE LISTING

```
<160> NUMBER OF SEQ ID NOS: 10

<210> SEQ ID NO 1
<211> LENGTH: 14
<212> TYPE: PRT
<213> ORGANISM: Artificial Sequence
<220> FEATURE:
<223> OTHER INFORMATION: amino acid sequence of TCR enriched clonotype
      1(1)

<400> SEQUENCE: 1

Cys Ala Ala Asn Arg Gly Ser Gly Tyr Ser Thr Leu Thr Phe
1               5                   10

<210> SEQ ID NO 2
<211> LENGTH: 13
<212> TYPE: PRT
```

```
<213> ORGANISM: Artificial Sequence
<220> FEATURE:
<223> OTHER INFORMATION: amino acid sequence of TCR enriched clonotype
      1(2)

<400> SEQUENCE: 2

Cys Ser Ala Arg Gly Glu Arg Gly Glu Lys Leu Phe Phe
1               5                   10

<210> SEQ ID NO 3
<211> LENGTH: 13
<212> TYPE: PRT
<213> ORGANISM: Artificial Sequence
<220> FEATURE:
<223> OTHER INFORMATION: amino acid sequence of TCR enriched clonotype
      2(1)

<400> SEQUENCE: 3

Cys Ala Ser Ser Ser Gly Gly Ser Tyr Ile Pro Thr Phe
1               5                   10

<210> SEQ ID NO 4
<211> LENGTH: 14
<212> TYPE: PRT
<213> ORGANISM: Artificial Sequence
<220> FEATURE:
<223> OTHER INFORMATION: amino acid sequence of TCR enriched clonotype
      2(2)

<400> SEQUENCE: 4

Cys Ala Ser Ser Leu Ala Gly Gly His Glu Thr Gln Tyr Phe
1               5                   10

<210> SEQ ID NO 5
<211> LENGTH: 13
<212> TYPE: PRT
<213> ORGANISM: Artificial Sequence
<220> FEATURE:
<223> OTHER INFORMATION: amino acid sequence of TCR enriched clonotype
      3(1)

<400> SEQUENCE: 5

Cys Ala Val Asn Ser Tyr Asn Thr Asp Lys Leu Ile Phe
1               5                   10

<210> SEQ ID NO 6
<211> LENGTH: 15
<212> TYPE: PRT
<213> ORGANISM: Artificial Sequence
<220> FEATURE:
<223> OTHER INFORMATION: amino acid sequence of TCR enriched clonotype
      3(2)

<400> SEQUENCE: 6

Cys Ala Thr Ser Arg Glu Glu Asp Asn Thr Tyr Glu Gln Tyr Phe
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: amino acid sequence of TCR enriched clonotype
      4(1)

<400> SEQUENCE: 7

Cys Ala Val Gly Gly Asn Glu Lys Leu Thr Phe
1               5                   10
```

```
<210> SEQ ID NO 8
<211> LENGTH: 15
<212> TYPE: PRT
<213> ORGANISM: Artificial Sequence
<220> FEATURE:
<223> OTHER INFORMATION: amino acid sequence of TCR enriched clonotype
      4(2)

<400> SEQUENCE: 8

Cys Ala Ser Ser Gln Gly Thr Gly Arg Ser Ser Pro Leu His Phe
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: amino acid sequence of TCR enriched clonotype
      5(1)

<400> SEQUENCE: 9

Cys Ala Ala Ser Ala Val Gly Gly Ala Gln Lys Leu Val Phe
1               5                   10

<210> SEQ ID NO 10
<211> LENGTH: 13
<212> TYPE: PRT
<213> ORGANISM: Artificial Sequence
<220> FEATURE:
<223> OTHER INFORMATION: amino acid sequence of TCR enriched clonotype
      5(2)

<400> SEQUENCE: 10

Cys Ala Thr Ser Arg Gly Thr Leu Tyr Gly Tyr Thr Phe
1               5                   10
```

TCR-ENRICHED CLONOTYPE, ACQUISITION METHOD AND USE THEREOF

CROSS REFERENCE TO RELATED APPLICATIONS

This application is a continuation-in-part of International Patent Application No. PCT/CN2020/105806, filed on Jul. 30, 2020, entitled "TCR-ENRICHED CLONOTYPE, ACQUISITION METHOD AND USE THEREOF", which is incorporated herein by reference in its entirety. This patent application also claims the benefits and priority of the following Chinese patent applications filed on May 23, 2020, including: Chinese Patent Application No. 202010444542.3 entitled "TCR-ENRICHED CLONOTYPE, ACQUISITION METHOD AND USE THEREOF", Chinese Patent Application No. 202010444541.9 entitled "TCR-ENRICHED CLONOTYPE, ACQUISITION METHOD AND USE THEREOF", Chinese Patent Application No. 202010445718.7 entitled "TCR-ENRICHED CLONOTYPE, ACQUISITION METHOD AND USE THEREOF", Chinese Patent Application No. 202010444548.0 entitled "TCR-ENRICHED CLONOTYPE, ACQUISITION METHOD AND USE THEREOF", and Chinese Patent Application No. 202010444546.1 entitled "TCR-ENRICHED CLONOTYPE, ACQUISITION METHOD AND USE THEREOF", the disclosures of which are incorporated by reference herein in their entirety or in part as part of the present application.

REFERENCE TO SEQUENCE LISTING

A computer readable TXT file entitled "Sequence Listing", that was created on Sep. 15, 2021, with a file size of 2,829 bytes, contains the sequence listing for this application, has been filed with this application, and is hereby incorporated by reference in its entirety.

TECHNICAL FIELD

The present disclosure relates to the technical field of biomedicine, and in particular to TCR-enriched clonotypes, an acquisition method and use thereof.

BACKGROUND ART

The outbreak of 2019-novel coronavirus (2019-nCOV) infection poses a serious threat to global public health. The disease caused by 2019-nCOV was officially named coronavirus disease 2019 (COVID-19) by the World Health Organization (WHO). COVID-19 is clinically manifested as pneumonia, fever, cough, muscle pain, fatigue, diarrhea, and even death in severe cases. The WHO report shows that 2019-nCOV has caused a worldwide pandemic. Vaccination is an effective means to prevent the outbreak of viral infections effectively, but there is no 2019-nCOV vaccine (hereinafter referred to as the COVID-19 vaccine) so far. In response to the fast-spreading 2019-nCOV in the public, the current treatment is still based on supportive care. Antiviral drugs, antibodies, and vaccines for COVID-19 are still in clinical trials and have not been successfully developed. Most patients are given the same symptomatic treatment as SARS back then, i.e., using hormones to suppress the inflammatory response caused by the immune system, but at the same time, the human body will become very fragile and be inevitably damaged. Therefore, it is an urgent need for effective vaccine development to curb the global outbreak of the virus.

T cell (antigen) receptor (TCR), as a characteristic marker on the surface of all T cells, binds to CD3 by non-covalent bonds to form a TCR-CD3 complex. The role of TCR is to recognize antigens. TCR is a heterodimer composed of two different peptide chains, i.e. a and B chains. Each peptide chain can be divided into variable region (V region), constant region (C region), and transmembrane region, and cytoplasmic region; the characteristic thereof is that the cytoplasmic region is very short. TCR molecules belong to the immunoglobulin superfamily, and antigen specificity thereof is present in the V region; each V region (Vα or Vβ) has three hypervariable regions, CDR1, CDR2, and CDR3, of which CDR3 has the largest variability that directly determines the antigen-binding specificity of the TCR. When TCR recognizes an MHC-antigen peptide complex, CDR1 and CDR2 recognize and bind to the side wall of an antigen-binding groove of an MHC molecule, and CDR3 directly binds to the antigen peptide.

SUMMARY

To achieve the above objective, the present disclosure provides TCR-enriched clonotypes, and amino acid sequences thereof are: CAANRGSGYSTLTF (SEQ ID NO: 1)_CSARGERGEKLFF (SEQ ID NO:2), CASSSGGSYIPTF (SEQ ID NO: 3)_CASSLAGGHETQYF (SEQ ID NO:4), CAVNSYNTDKLIF (SEQ ID NO: 5)_CATSREEDNTYEQYF (SEQ ID NO:6), CAVGGNEKLTF (SEQ ID NO: 7)_CASSQGTGRSSPLHF (SEQ ID NO:8), and CAASAVGGAQKLVF (SEQ ID NO: 9)_CATSRGTLYGYTF (SEQ ID NO:10), respectively.

The present disclosure further provides a method for acquiring the above TCR-enriched clonotypes, including the following steps:

S1, collecting peripheral blood mononuclear cell samples from a cured patient with viral infection;

S2, conducting TCR/BCR V(D)J immune repertoire sequencing analysis on a collected sample to find a shared CDR3 variable region; and S3, detecting the distribution of cell clonotypes with high enrichment degree in the cured patient with viral infection, thereby further obtaining the TCR-enriched clonotypes.

Herein, the TCR-enriched clonotypes having the amino acid sequences of CAANRGSGYSTLTF (SEQ ID NO: 1)_CSARGERGEKLFF (SEQ ID NO: 2) and CAVGGNEKLTF (SEQ ID NO: 7)_CASSQGTGRSSPLHF (SEQ ID NO: 8) are enriched in a cell cluster of effector-memory CD4+ T cells, and the TCR-enriched clonotypes having the amino acid sequences of CASSSGGSYIPTF (SEQ ID NO: 3)_CASSLAGGHETQYF (SEQ ID NO: 4), CAVNSYNTDKLIF (SEQ ID NO: 5)_CATSREEDNTYEQYF (SEQ ID NO: 6) and CAASAVGGAQKLVF (SEQ ID NO: 9)_CATSRGTLYGYTF (SEQ ID NO: 10) are enriched in a cell cluster of effector CD8+ T cells.

The present disclosure further provides use of the TCR-enriched clonotypes in guiding vaccine development.

Herein, the vaccine is a 2019-nCOV vaccine.

Beneficial technical effects are as follows: Disclosed are TCR-enriched clonotypes, an acquisition method and use thereof. In the present disclosure, the amino acid sequences of the TCR-enriched clonotypes are: CAANRGSGYSTLTF (SEQ ID NO: 1)_CSARGERGEKLFF (SEQ ID NO: 2), CASSSGGSYIPTF (SEQ ID NO:

3)_CASSLAGGHETQYF (SEQ ID NO: 4), CAVNSYN-TDKLIF (SEQ ID NO: 5)_CATSREEDNTYEQYF (SEQ ID NO: 6), CAVGGNEKLTF (SEQ ID NO: 7)_CASSQGT-GRSSPLHF (SEQ ID NO: 8), and CAASAVGGAQKLVF (SEQ ID NO: 9)_CATSRGTLYGYTF (SEQ ID NO: 10), respectively. Moreover, the above TCR-enriched clonotypes are of positive significance for specifically recognized antigenic epitopes through the shared CDR3 variable region. Therefore, the TCR-enriched clonotypes can be used to guide vaccine development and provide direction and theoretical basis for vaccine development and research.

DETAILED DESCRIPTION OF THE EMBODIMENTS

To enable those skilled in the art to better understand the technical solutions of the present disclosure, the present disclosure will be further described in detail below with reference to the accompanying drawings.

The material within sequence listing text file named sequencelisting.txt, which was created on Aug. 24, 2021 and is 2,829 bytes is incorporated by reference herein in its entirety.

The present disclosure provides TCR-enriched clonotypes, and the amino acid sequences thereof are: CAANRGSGYSTLTF (SEQ ID NO: 1)_CSARG-ERGEKLFF (SEQ ID NO: 2), CASSSGGSYIPTF (SEQ ID NO: 3)_CASSLAGGHETQYF (SEQ ID NO: 4), CAVN-SYNTDKLIF (SEQ ID NO: 5)_CATSREEDNTYEQYF (SEQ ID NO: 6), CAVGGNEKLTF (SEQ ID NO: 7)_CASSQGTGRSSPLHF (SEQ ID NO: 8), and CAASAVGGAQKLVF (SEQ ID NO: 9)_CATSRGT-LYGYTF (SEQ ID NO: 10), respectively.

The present disclosure further provides a method for acquiring the above TCR-enriched clonotype, including the following steps:
S1, collecting peripheral blood mononuclear cell samples from a cured patient with viral infection;
S2, conducting TCR/BCR V(D)J immune repertoire sequencing analysis on a collected sample to find a shared CDR3 variable region; and
S3, detecting the distribution of cell clonotypes with high enrichment degree in the cured patient with viral infection, thereby further obtaining the TCR-enriched clonotypes.

Figure 1:
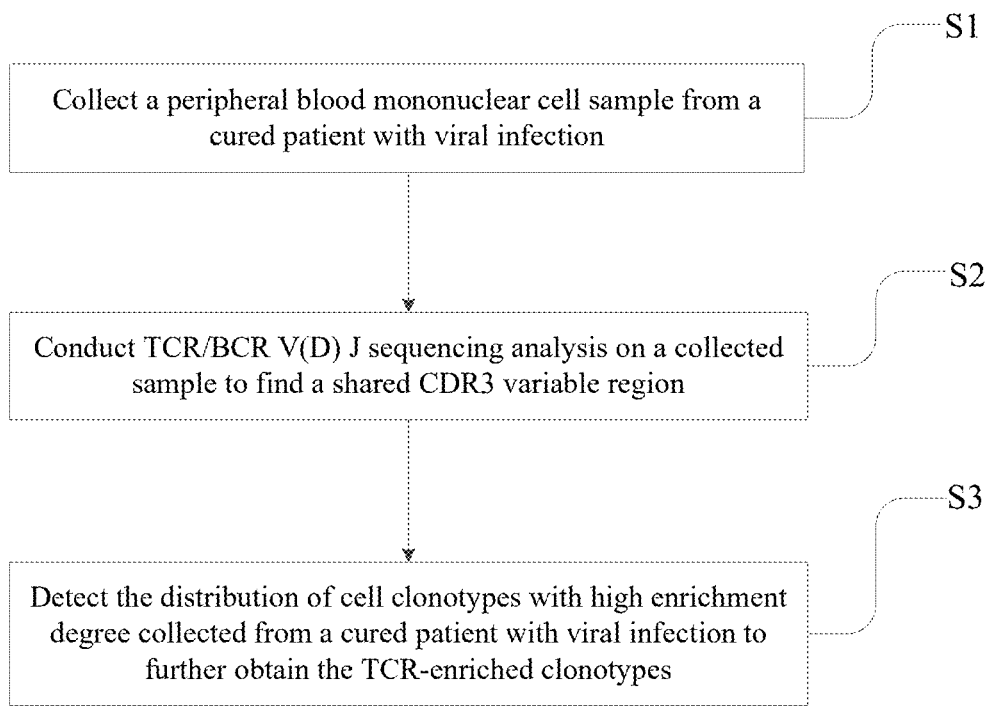
FIG. 1 is a flow chart of a method for acquiring TCR-enriched clonotypes in the present disclosure.

The flowchart of the acquisition method of the present disclosure is shown in FIG. 1.

The method for acquiring the above TCR-enriched clonotypes specific included the following steps:

1. Single Cell Transcriptome and TCR Sequencing of Peripheral Blood Mononuclear Cells Separately, 2 ml of peripheral blood was drawn from normal patients (control) and cured COVID-19 patients, and peripheral blood mononuclear cells (PBMCs) were isolated. The single cell concentration was approximately 1,000 cells/µl, and approximately 20,000-25,000 cells were added into a Chromium Next GEM Chip Single Cell Kit according to the concentration. A single cell was lysed and reverse transcribed; single cell droplets formed in the chip were disrupted and purified, and PCR amplification was conducted in the presence of universal primers; the resulting cDNA product was used to construct a library for gene expression and TCR sequencing. Then the cDNA library was sequenced on the Illumina NovaSeq 6000 System.

2. Single Cell Cluster Analysis

The raw data of single cell RNA sequencing were aligned with human reference genome hg38, and quantified by Cellranger 3.0.1 pipeline (10× Genomics) to generate an expression matrix. The cells were subjected to a comprehensive cluster analysis using Seurat package (version 3.1.2); the cell count data were normalized according to the expression matrix and logarithmically transformed by using NormalizeData function. "FindVariableGenes" function was used to obtain 2,000 highly variable genes for principal component analysis (PCA). Thirty PCs were selected for UMAP analysis. Subsequently, the resolution of the clustering parameter in Seurat's FindClusters function was set to 0.3 to recognize cell subsets. Among these subsets, using FindMarkers and findalmarkers functions in Seurat package, differentially expressed genes (DEGs) were identified by the MAST method in the single-cell differential gene expression analysis. Significant DEGs were identified by an average logarithmic fold change (avg.logFC) and a P value adjusted (p.val.adj.). Enriched CDR3 sequences located and identified by the single cell cluster analysis were derived from the species of the immune cell subset.

3. TCR Identification

Based on TCR V(D)J sequencing, the clonotypes were identified and calculated by Loupe V(D)J Browser (V3.0.0) developed by 10× Genomics. Identifying and calculating the abundance of clonotypes formed by CDR3 sequences of all different combinations of TRA and TRB by software, using the percentage of clonotype cells with different CDR3 sequences in total cell count (more than 3%) as a threshold, TCR-enriched clonotypes were screened and identified, and the corresponding enriched CDR3 sequences were obtained. Meanwhile, because each cell has a unique identification tag, it can be distinguished that cells with different CDR3 sequences are from different immune cell subsets.

Identification Process and Results

After cluster analysis of the acquired single cell sequencing data, 20 different cell subsets were isolated finally; these cell subsets were clustered and identified, and TCR clonotypes were further identified as follows:

1. Identification Results of Immune Cell Subsets

Figure 4:
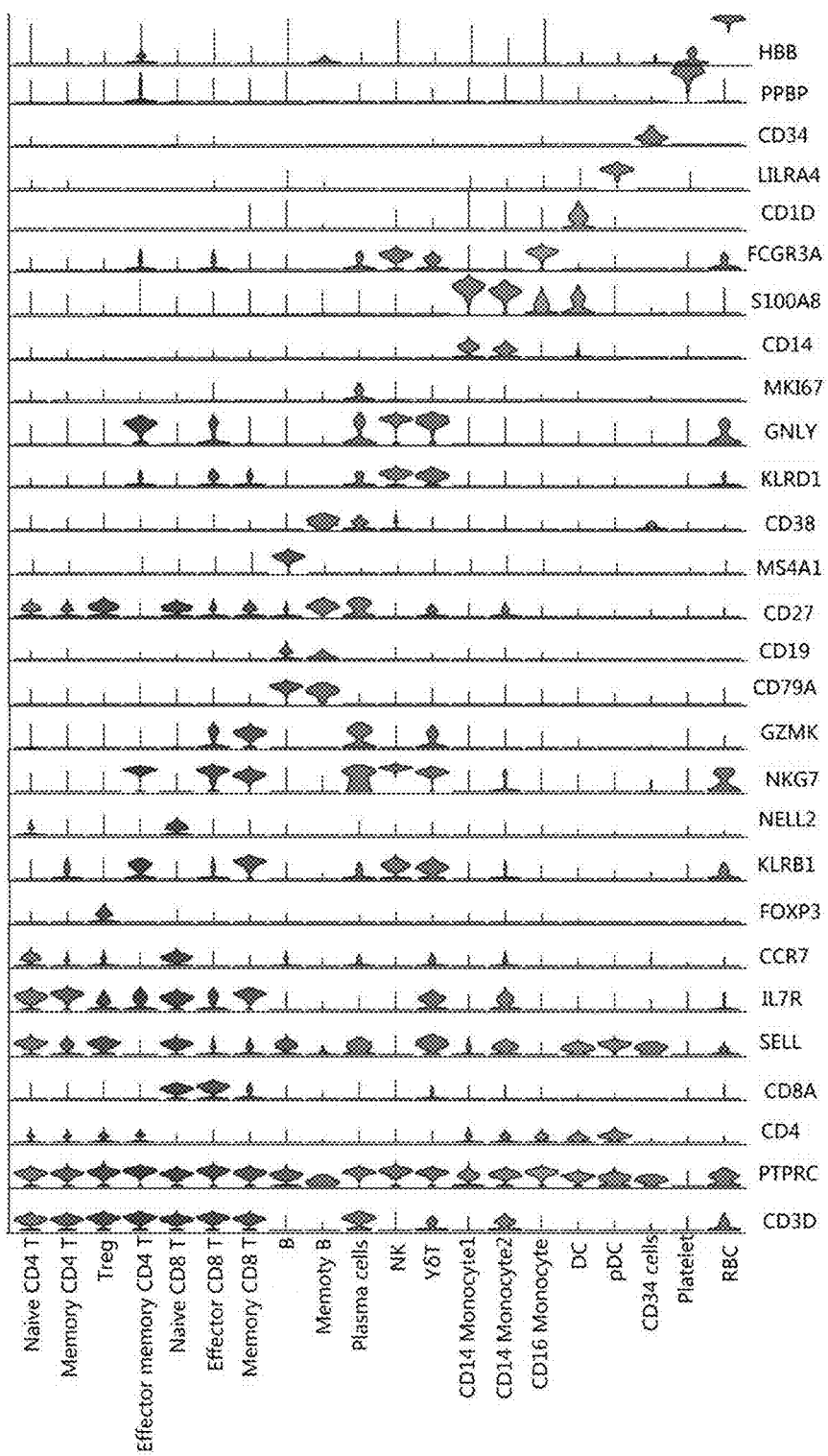
FIG. 4 illustrates molecular markers selected in the identification of immune cell subsets and final identified immune cell subset results.

In view of different cell types in peripheral blood mononuclear cells, different immune cell subsets were identified by the expression of cell surface markers, Cell marker genes, in different immune cell subsets. The Cell markers used and final identified immune cell subset results are shown in FIG. 4. From FIG. 4, positive molecular markers of effector-memory $CD4^+$ T cells include CD3D+PRPRC+CD4+IL7R+

KLRB1+NKG7+GNLY+, and positive molecular markers of effector CD8+ T cells include CD3D+PRPRC+CD8A+SELL+IL7R+KLRB1+NKG7+GZMK+CD27+KLRD1+.

This indicates that the present disclosure successfully screens and obtains an effector-memory CD4+ T cell subset and effector CD8+ T cells.

Figure 5:
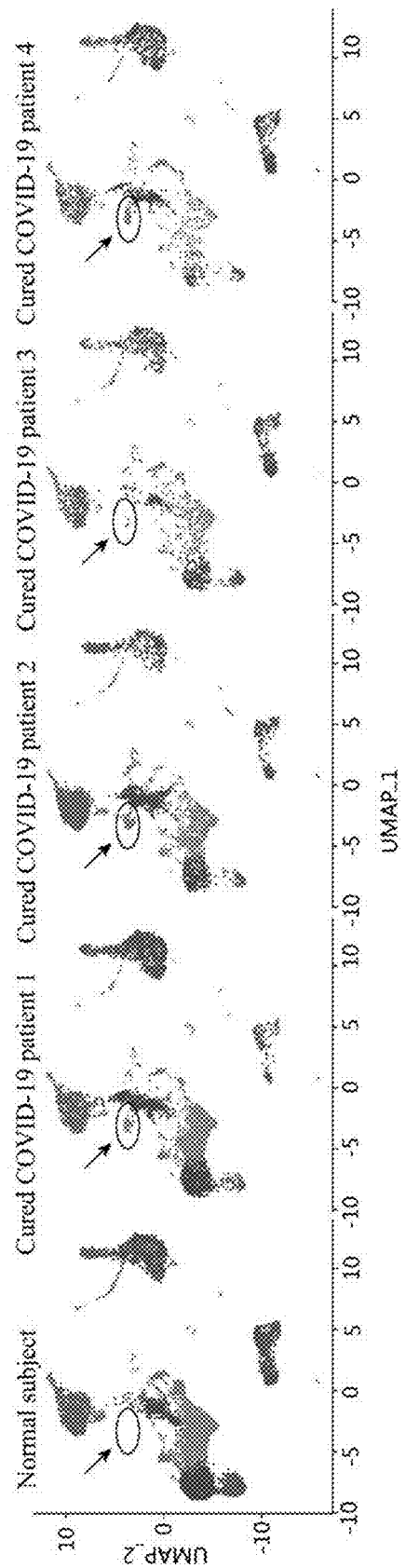
FIG. 5 illustrates comparative results of effector-memory CD4+ T cell subsets specifically appeared in all cured COVID-19 patients.

Herein, the effector-memory CD4+ T cell subset is a cell subset specifically present in all cured COVID-19 patients, and the amount thereof is very low in healthy control peripheral blood (FIG. 5). Because the effector-memory CD4+ T cells mainly respond to cytokine-driven cytotoxic immune response to protect against reoccurring infections. Therefore, compared with normal subjects (healthy subjects), the appearance and sharp increase of the effector-memory CD4+ T cell subset indicates that COVID-19 patients have a specific immune cell subset against the reoccurring infections of 2019-nCoV.

2. Identification of CDR3 Sequences of Specific TCR Clonotypes

TCR, an antigen receptor on the surface of a T cell, is used for T cell-specific antigen recognition and is the first crucial molecule that produces an immune response after T cell-specific antigen recognition. The V-(D)-J-C gene in TCR is rearranged to form different combinations and thus forming different clonotypes, wherein the TCR hypervariable region, complementarity-determining region 3 in the VB gene (CDR3, composed of V, D, and J regions) is the most principal antigen specifically recognized by T cells and a characteristic of immune response. If a cloning change in a CDR3 region of a TCR VB family is detected, this indicates that a T cell induces a specific response to an antigen. Mature T cells constitute a diverse T cell repertoire and form a diverse T cell CDR3 receptor repertoire.

Figure 2:
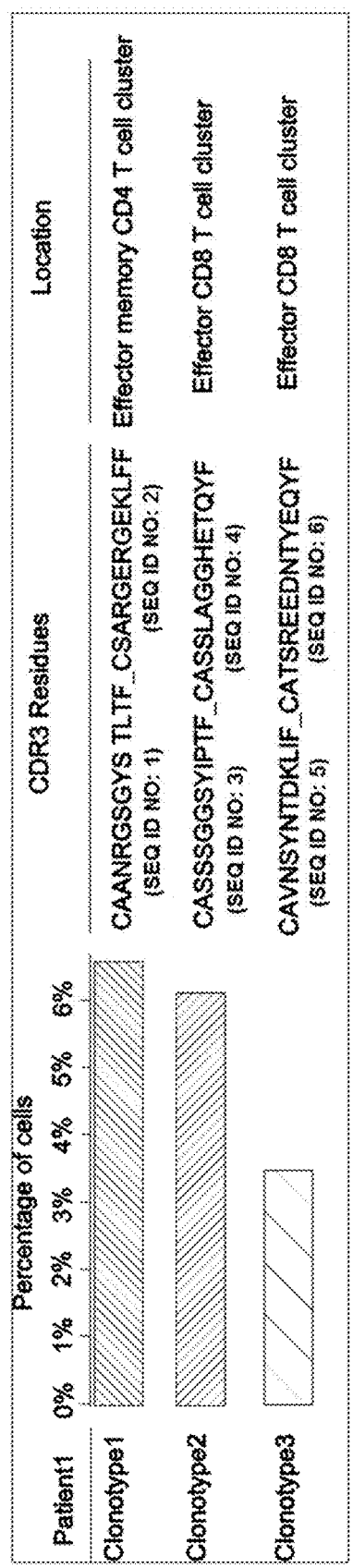
FIG. 2 is a schematic diagram of the location of the TCR-enriched clonotypes in patient 1 and the enrichment degree thereof in TCR cells in the present disclosure.
Figure 3:
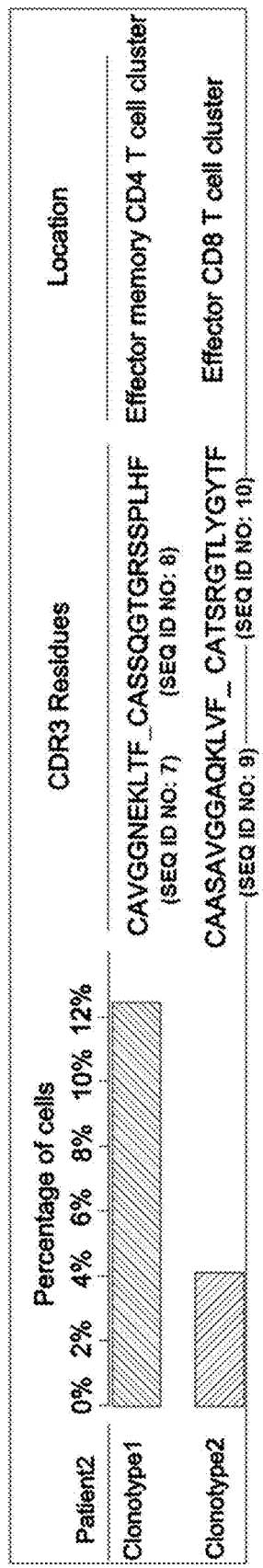
FIG. 3 is a schematic diagram of the location of the TCR-enriched clonotypes in patient 2 and the enrichment degree thereof in TCR cells in the present disclosure.
Figure 6:
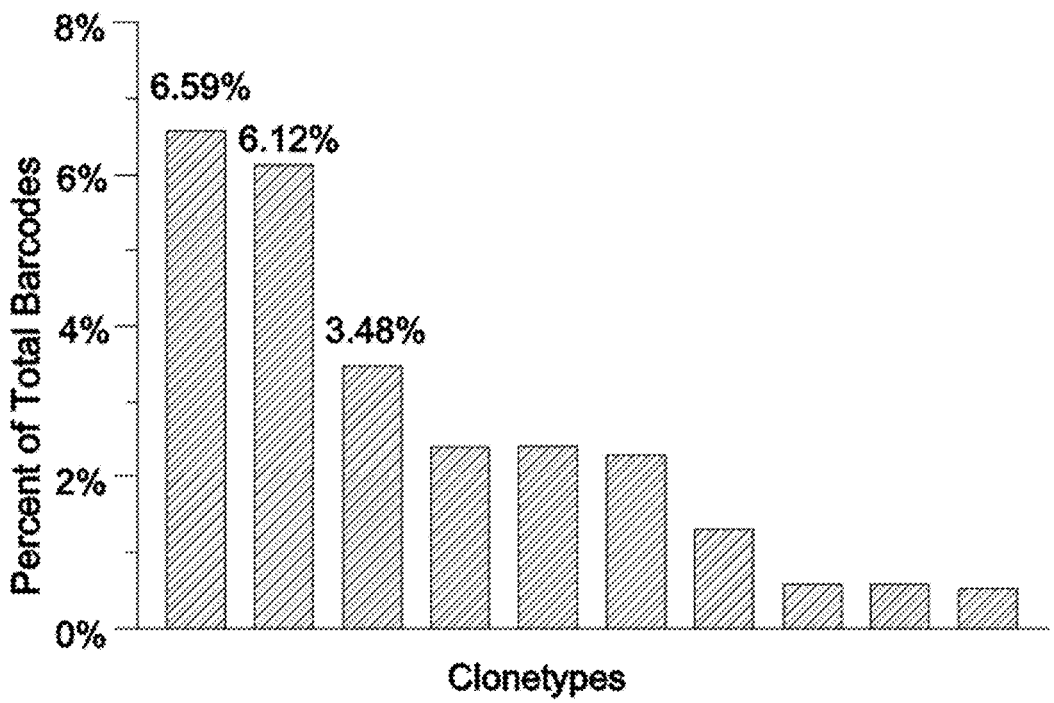
FIG. 6 illustrates a statistical result of the percentages of TCR clonotype cells in different CDR3 sequences of cured COVID-19 patient 1.
Figure 7:
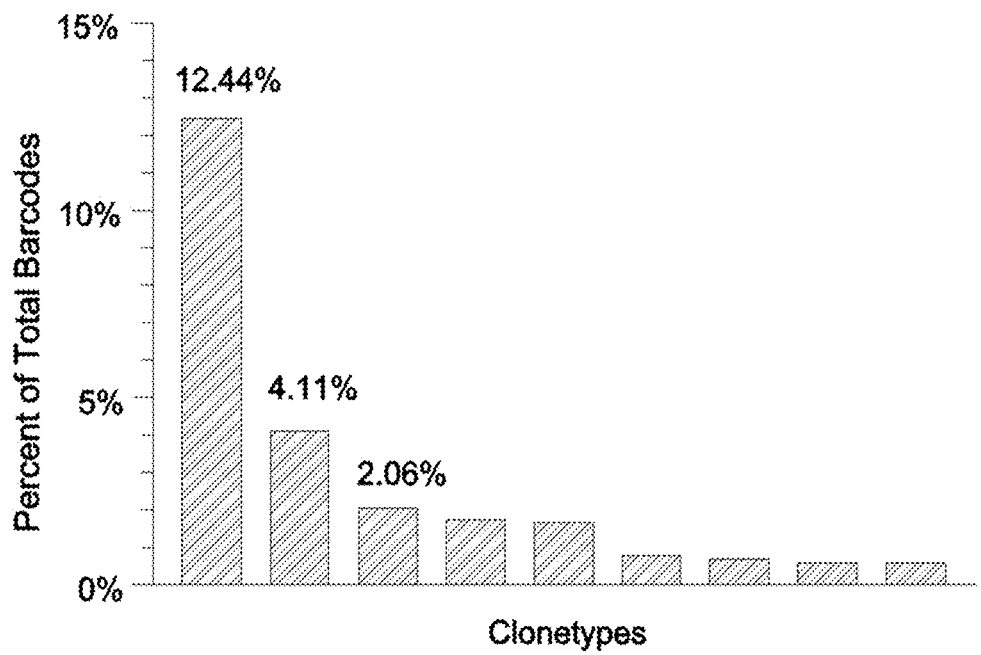
FIG. 7 illustrates a statistical result of the percentages of TCR clonotype cells in different CDR3 sequences of cured COVID-19 patient 2.

To determine whether cloning cell subsets with the same CDR3 sequence were formed, according to the sequence alignment of single cell TCR sequencing results, the percentage of cells with the same CDR3 sequence in total cells was counted, and when the percentage exceeded the threshold (3%), then cloning formation was determined. Finally, six pairs of enriched cell clones of CDR3 sequence were identified in two COVID-19 patients (cured COVID-19 patients 1 and 2) (see the results of the first three groups in FIGS. 6 and 7, wherein the barcodes height indicates the percentage of each pair of cells with enriched CDR3 sequence). By identifying the cell label where the CDR3 sequence was located, CAANRGSGYSTLTF (SEQ ID NO: 1)_CSARGERGEKLFF (SEQ ID NO: 2) sequence (clonotype 1) and CAVGGNEKLTF (SEQ ID NO: 7)_CASSQGTGRSSPLHF (SEQ ID NO: 8) (clonotype 4) were derived from the effector-memory CD4+ T cell subsets specifically appeared in cured COVID-19 patients, and the percentage of cells with the CAANRGSGYSTLTF (SEQ ID NO: 1)_CSARGERGEKLFF (SEQ ID NO: 2) sequence (clonotype 1) reached 6.59% (see the left first barcodes result in FIG. 6, and FIG. 2). The percentage of cells with the CAVGGNEKLTF (SEQ ID NO: 7)_CASSQGTGRSSPLHF (SEQ ID NO: 8) sequence (clonotype 4) reached 6.86% (FIG. 3); meanwhile, the CAVGGNEKLTF (SEQ ID NO: 7)_CASSQGTGRSSPLHF (SEQ ID NO: 8) sequence (clonotype 4) was further detected as another type, and the percentage of cells was 5.85% (see the left second barcodes result in FIG. 7), corresponding the most frequent two clonotypes in patient 2 (6.86% and 5.58%, respectively). There were two different base sequences in the nucleotide sequences of the two clonotypes, thus they were divided into two clonotypes. However, the amino acid sequences encoded by the clonotypes were identical, and the epitope sequences identified were also identical. In view of this, the two clonotypes that were the most frequent in patient 2 were regarded as the same clonotype (clonotype 4), with a frequency ration of 12.44%. CASSSGGSYIPTF (SEQ ID NO: 3)_CASSLAGGHETQYF (SEQ ID NO: 4) sequence (clonotype 2), CAVNSYNTDKLIF (SEQ ID NO: 5)_CATSREEDNTYEQYF (SEQ ID NO: 6) sequence (clonotype 3), and CAASAVGGAQKLVF (SEQ ID NO: 9)_CATSRGTLYGYTF (SEQ ID NO: 10) sequence (clonotype 5) were derived from effector CD8+ T cells, the percentages of which were 6.12%, 3.48%, and 4.11%, respectively (FIGS. 2 and 3).

In this example, peripheral blood mononuclear cells from four cured patients infected with 2019-nCOV were selected as samples, and the samples collected were subjected to TCR/BCR V(D)J immune repertoire sequencing analysis. Sequencing analysis results showed no shared cell clonotype, but there was a shared CDR3 variable region. Through the detection of the distribution of cell clonotypes with high enrichment degree in patients with viral infection, TCR-enriched clonotypes enriched in the effector CD8+ T cell clusters and having amino acid sequences of CASSSGGSYIPTF (SEQ ID NO: 3)_CASSLAGGHETQYF (SEQ ID NO: 4), CAVNSYNTDKLIF (SEQ ID NO: 5)_CATSREEDNTYEQYF (SEQ ID NO: 6), and CAASAVGGAQKLVF (SEQ ID NO: 9)_CATSRGTLYGYTF (SEQ ID NO: 10) were acquired, and TCR-enriched clonotypes enriched in the effector-memory CD4+ T cell cluster and having amino acid sequences of CAANRGSGYSTLTF (SEQ ID NO: 1)_CSARGERGEKL and CAVGGNEKLTF (SEQ ID NO: 7)_CASSQGTGRSSPLHF (SEQ ID NO: 8). Therefore, the TCR-enriched clonotypes have a positive effect on specifically recognized antigen epitopes through a shared CDR3 variable region.

Because CD4+ T cells specifically recognized the exogenous target cells or molecules through TCR, the antigen polypeptides processed by antigen-presenting cells and presented by surface MHC-II molecules quickly triggered the immune function of CD4+ T cells killing exogenous target cells. Considering that the TCR sequence identified in the present disclosure was the shared CDR3 clonotype identified and found in cured COVID-19 patients and that this clonotype specifically appeared in the effector-memory CD4+ T cells in cured patients rather than in normal subjects, it can be inferred that the clonotype is specific to recognize the 2019-nCOV antigen or the cells infected with 2019-nCoV.

It has been reported in the prior art that the CDR3 has the specificity of antigenic epitope recognition. For example, prior art 1 reported that T cell receptor (TCR) nucleotide sequences were often generated during analyses of T cell responses to pathogens or autoantigens. The most important region of the TCR was the third complementarity-determining region (CDR3), of which nucleotide sequence was unique to each T cell clone. The CDR3 can be interacted with the peptide and thus was important for recognizing pathogen or autoantigen epitopes (prior art 1: A clonotype nomenclature for T cell receptors, Immunogenetics. 2009 July; 61 (7): 493-502). Prior art 2 reported that all rearranging antigen receptor genes had one or two highly diverse complementarity-determining regions (CDRs) among the six that typically formed the ligand binding surface. In the case of antibodies, diversity at one of these regions, CDR3 of the V(H) domain, was sufficient to permit other identical IgM molecules to distinguish between a variety of hapten and protein antigens. Furthermore, it was found that somatic mutation could allow such antibodies to achieve surprisingly high affinities. These results were consistent with a model in which the highly diverse CDR3 loops were the key determinant of specificity in antigen recognition in both TCRs and antibodies, whereas the germline-encoded CDR1 and CDR2 sequences were much more cross-reactive (prior art 2: Diversity in the CDR3 region of V(H) is sufficient for most antibody specificities, Immunity 2000 July; 13 (1): 37-45). Prior art 3 reported that TCR was a complex heterodimer, which can recognize fragments of antigens as peptides and bound to major histocompatibility complex molecules. The TCR α and β chains possessed three hypervariable regions termed complementarity-determining regions (CDR1, 2 and 3). CDR3 was responsible for recognizing processed antigen peptides. Immunoscope spectratyping was a simple technique for analyzing CDR3 polymorphisms and sequence length diversity, so as to investigate T cell function and the pattern of TCR utilization. The present study employed this technique to analyze CDR3 polymorphisms and the sequence length diversity of TCR α and β chains in porcine $CD4^+$ and $CD8^+$ T cells. Polymerase chain reaction products of 19 TCR α variable regions (AV) and 20 TCR β variable regions (BV) gene families obtained from the $CD4^+$ and $CD8^+$ T cells revealed a clear band following separation by 1.5% agarose gel electrophoresis, and each family exhibited >8 bands following separation by 6% sequencing gel electrophoresis. CDR3 spectratyping of all identified TCR AV and BV gene families in the sorted $CD4^+$ and $CD8^+$ T cells by GeneScan demonstrated a standard Gaussian distribution with >8 peaks. CDR3 in $CD4^+$ and $CD8^+$ T cells demonstrated different expression patterns (prior art 3: Analysis of the CDR3 length repertoire and the diversity of T cell receptor a and B chains in swine $CD4^+$ and $CD8^+$ T lymphocytes, Mol Med Rep. 2017 July; 16 (1): 75-86). Prior art 4 further reported the possibility to simultaneously assay T-cell specificity to large sets of antigens and the T-cell receptor sequence in high-throughput single-cell experiments. Leveraging this new type of data, a collection of deep learning architectures were proposed and tested to stimulate T cell specificity in single cell. In agreement with previous results, it was found that models that treated antigens as categorical outcome variables outperformed those that modeled the TCR and antigen sequence jointly. Moreover, it was shown that the variability in single-cell immune repertoire screens could be mitigated by modeling cell-specific covariates. The number of bounded pMHC complexes could be predicted in a continuous mode, providing a gateway to disentangle the cell-to-dextramer binding strength and the receptor-to-pMHC affinity. These models were provided in the Python package TcellMatch to allow imputation of antigen specificities in single-cell RNA-seq studies on T cells without the need for MHC staining (prior art 4: Predicting antigen specificity of single T cells based on TCR CDR3 regions, Mol Syst Biol (2020) 16: e9416).

In this example, the above TCR-enriched clonotypes are used to guide vaccine development, especially to guide the development of 2019-nCOV vaccines. In the present disclosure, the results predicted by protein-protein interactions show that the TCR-enriched clonotypes have a positive effect on specifically recognized antigen epitopes through the shared CDR3 variable region. Therefore, the TCR-enriched clonotypes can be used to guide vaccine development and provide direction and theoretical basis for vaccine development and research.

To further understand the specific immune response to SARS-Cov2 infection, paired TCR/BCR V(D)J immune repertoire sequencing that links the diversity of the receptor clonotype to the gene expression profile of each cell was conducted in this example. Five high-frequency T cell clonotypes were found when scanning the frequencies of T and B cell clonotypes in cured patients. Moreover, more than 3% of T cells were detected in total detected cells of each cured patient. It could therefore be determined that T cells play a crucial role in viral clearance. Two of the five T cell clonotypes discovered were enriched in the effector-memory $CD4^+$ T cell cluster, and the other three ones were enriched in the effector $CD8^+$ T cell cluster, further demonstrating the specific immune response of these two T cell subsets to SARS-Cov2 reoccurring. Therefore, the TCR-enriched clonotypes disclosed in the present disclosure can be used for guiding vaccine development and provide direction and theoretical basis for vaccine development and research.

The TCR-enriched clonotypes, the acquisition method and the use thereof provided by the present disclosure are described in detail above. Specific cases are used herein to illustrate the principle and implementation of the present disclosure, and the description of the above examples is only intended to help understand the core idea of the present disclosure. It should be noted that several improvements and modifications may also be made by those of ordinary skill in the art without departing from the principle of the present disclosure and fall within the protection scope of the claims of the present disclosure.

What is claimed is:

1. A method for acquiring TCR-enriched clonotypes, wherein the amino acid sequences of each pair of the TCR-enriched clonotypes are set forth in SEQ ID NO: 1 and SEQ ID NO: 2, SEQ ID NO: 3 and SEQ ID NO: 4, SEQ ID NO: 5 and SEQ ID NO: 6, SEQ ID NO: 7 and SEQ ID NO: 8, or SEQ ID NO: 9 and SEQ ID NO: 10, respectively;

and wherein the acquisition method comprises the following steps:

collecting peripheral blood mononuclear cell samples from a cured patient with viral infection;

conducting TCR/BCR V(D)J immune repertoire sequencing analysis on a collected sample to find a shared CDR3 variable region; and detecting the distribution of cell clonotypes with high enrichment degree in the cured patient with viral infection to further obtain the TCR-enriched clonotypes.

2. The method for acquiring TCR-enriched clonotypes according to claim 1, wherein the TCR-enriched clonotypes having the amino acid sequences set forth in SEQ ID NO: 1 and SEQ ID NO: 2 and SEQ ID NO: 7 and SEQ ID NO: 8 are enriched in a cell cluster of effector-memory CD4$^+$ T cells, and the TCR-enriched clonotypes having the amino acid sequences set forth in SEQ ID NO: 3 and SEQ ID NO: 4 SEQ ID NO: 5 and SEQ ID NO: 6 and SEQ ID NO: 9 and SEQ ID NO: 10 are enriched in a cell cluster of effector CD8$^+$ T cells.

* * * * *